United States Patent [19]

Leigh et al.

[11] Patent Number: 4,711,637
[45] Date of Patent: Dec. 8, 1987

[54] SYRINGE LOCK

[75] Inventors: Harold G. Leigh, Creve Coeur; Eli Schachet, St. Louis, both of Mo.

[73] Assignee: Baxter Travenol Laboratories, Inc., Deerfield, Ill.

[21] Appl. No.: 825,823

[22] Filed: Feb. 4, 1986

[51] Int. Cl.$^4$ ............................................. A61M 5/315
[52] U.S. Cl. .................................................. 604/220
[58] Field of Search ............... 604/220, 218, 222, 110, 604/111, 210

[56] References Cited

U.S. PATENT DOCUMENTS

| | | | |
|---|---|---|---|
| 772,114 | 10/1904 | Pappenheim | 604/220 |
| 2,869,541 | 1/1959 | Helmer et al. | 604/210 |
| 3,747,812 | 7/1973 | Karman et al. | 604/220 X |
| 4,592,746 | 6/1986 | Burkholder et al. | 604/220 |

FOREIGN PATENT DOCUMENTS

| | | | |
|---|---|---|---|
| 266921 | 2/1928 | Fed. Rep. of Germany | 604/220 |
| 1287742 | 1/1969 | Italy | 604/220 |

Primary Examiner—John D. Yasko
Attorney, Agent, or Firm—Roger A. Williams; Paul C. Flattery; Robert E. Hartenberger

[57] ABSTRACT

A lock for a syringe which typically may be used with an aspirating biopsy needle. A malleable sheet defining a central, cutaway portion extending through the edge of the sheet and having foldable tabs positioned on the outer edge of the sheet is carried on a syringe barrel and may be used to lock the syringe plunger in a predetermined position. Thus a vacuum may be drawn in the syringe by the plunger with the plunger then being locked to provide suction to the aspirating biopsy needle.

12 Claims, 5 Drawing Figures

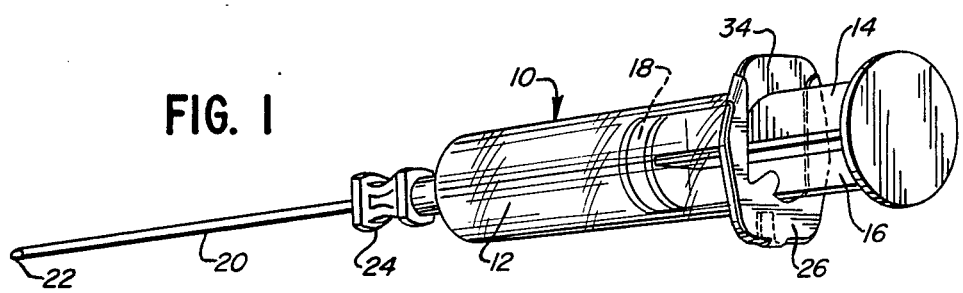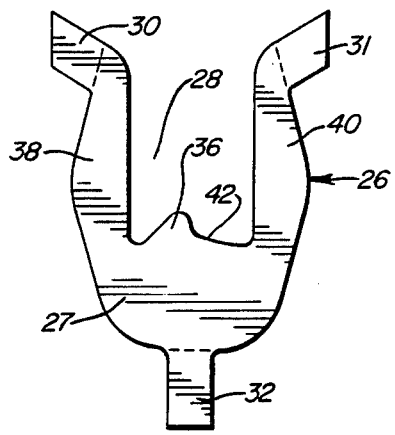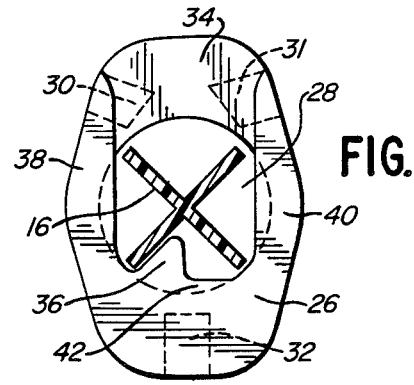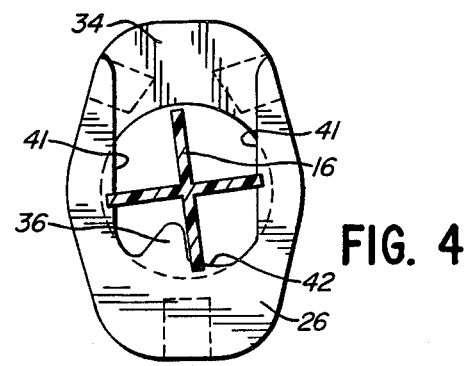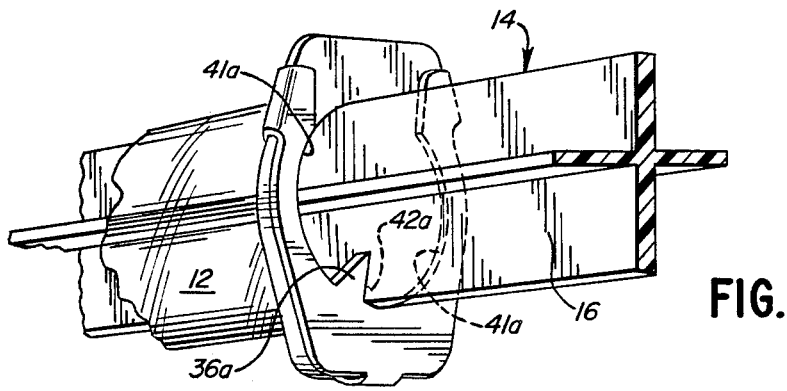

SYRINGE LOCK

TECHNICAL FIELD

Various designs of aspirating biopsy needles are used for taking in vivo internal tissue samples, for example a liver or kidney sample.

The biopsy needle, typically containing a stylet, is inserted into the patient until its point is just short of the region where the sample is to be taken.

The stylet is then removed from the needle, and a syringe of conventional design attached. One may then create a suction or reduced pressure through the bore of the aspirating biopsy needle by drawing back on the plunger of the syringe. One then advances the biopsy needle through the tissue from which the sample is to be taken. The suction encourages a small column of tissue to enter the bore of the aspirating biopsy needle to facilitate collection of the tissue sample. After the tissue sample has been collected, the plunger may be advanced again to cause it to be expelled from the biopsy needle into a collection vessel.

As the plunger of the syringe is retracted to create the suction pressure it will have a natural tendency to spontaneously advance again because of the suction pressure created. Thus, various syringe locks have been designed to hold the syringe plunger in retracted position, to provide a long-lasting suction pressure without requiring the user to hold the plunger in its retracted position.

The prior locking devices which have been used require either that the syringe, plunger or barrel be especially modified, and/or that the plunger, with its sealing piston attached, must be distorted as the plunger is forced past the locking device while being assembled with the syringe barrel by insertion therein. This is an inconvenient technique, and can result in distortion of part diameter, causing leakage, and even breakage of the parts.

Also, some existing syringe lock devices can only be locked at a single position, or can only be locked in predetermined, incremental positions. Also, other disadvantages are found in the prior art syringe locks.

In accordance with this invention, a locking device is provided which may be applied to a standard disposable syringe without requiring removal of the plunger from the syringe barrel or modification of the syringe itself to apply it.

The syringe lock of this invention permits the plunger to be locked in any desired position with respect to the barrel.

Likewise, the simple device of this invention does not require complex manipulation to be used, contrary to some of the prior art devices, where the user must operate a special lever, or slide a separate mechanism in place to lock the syringe. By this invention, a simple rotation of the plunger causes locking and unlocking thereof.

The device of this invention may also have a positive stop in both locking and unlocking to prevent the device from being twisted too far to unlock again, when it is desired to lock by twisting. Furthermore, the device of this invention may be used with most designs of existing disposable syringes, particularly essentially all of them in which the plunger has a section comprising radially extending vanes.

DESCRIPTION OF THE INVENTION

In accordance with this invention a lock for a syringe is provided which comprises a single sheet, said sheet defining a central, cutaway portion extending through the edge of the sheet. The sheet is typically made of metal, although certain non-resilient but typically flexible plastics may be used if desired. Specifically, copper-containing alloys such as malleable brass or bronze may be used, or aluminum alloys and the like.

The sheet carries foldable tab means positioned on the outer edge of the sheets. As the result of this, a syringe plunger comprising radially extending vanes can be placed to extend through the central, cutaway portion of the sheet. The tab means may then be secured by folding to a syringe barrel, and specifically a flange carried by the syringe barrel, in such a manner that rotation of the plunger in one direction causes at least one sheet edge defining the central, cutaway portion to dig into a vane of the plunger. This provides retention of the plunger and barrel in a fixed position relative to each other. Thus, the plunger may be drawn outwardly to create a suction pressure, and then rotated to retain the plunger in such drawn out position.

To release the plunger from its fixed position, one may rotate the retained plunger in the opposite direction to free it from its retained relation.

The sheet may typically be of generally U-shape, and may define a protrusion extending into the cutaway portion to serve as rotational stop means to limit free rotation of the plunger. Thus one cannot accidentally rotate the plunger into locked, retaining relation with the syringe lock and then accidentally overrotate the plunger, to cause it to disengage from its locking relation.

Typically, the tab means may comprise a foldable first and second tab, positioned respectively at the end of each arm of the U-shaped sheet, plus a third, foldable tab positioned at the end of the sheet opposed to the first and second tabs. These tabs fold around the rear flange of a conventional syringe for retention thereon.

A sryinge which carries the syringe lock of this invention may be used in any way desired, but particularly with an aspirating biopsy needle, in which the plunger of the syringe may be retracted to create a reduced pressure within the syringe, and locked in such position by means of this invention for efficient and effective collection of tissue samples.

DESCRIPTION OF THE DRAWINGS

Referring to the drawings,

FIG. 1 is a perspective view of a syringe carrying the lock of this invention, said syringe being attached to a biopsy needle;

FIG. 2 is a plan view of the lock of this invention prior to attachment to a syringe;

FIG. 3 is a plan view of the lock of FIG. 1 shown attached to a syringe, with the syringe plunger shown in transverse section and shown in a rotational position permitting free slidability thereof;

FIG. 4 is a view similar to that of FIG. 3, but showing the plunger rotated into locked position; and FIG. 5 is an enlarged detailed fragmentary perspective view of an alternative embodiment of the lock of this invention carried on a syringe.

DESCRIPTION OF SPECIFIC EMBODIMENTS

Referring to FIGS. 1 through 4, syringe 10 may be of conventional design, carrying a syringe barrel 12 and syringe plunger 14. Plunger 14 can be seen to comprise almost most of its length a plurality of radially extending vanes 16 and also a conventional sliding seal member 18.

Syringe 10 is shown to be attached to an aspirating biopsy needle 20, which also may be of conventional design. In typical use, biopsy needle 20 is equipped with a stylet through its bore, so that the needle can be advanced through tissue without the tubular needle becoming filled with unwanted tissue. Then, when the forward end 22 of biopsy needle 20 is advanced to the desired position, stylet may be removed, and syringe 10 attached to rear end 24 of biopsy needle 20.

At this point, plunger 14 is withdrawn to create a suction pressure inside of syringe barrel 12 and through the bore of biopsy needle 20. In accordance with this invention, lock 26 is provided to lock withdrawn plunger 14 into fixed relation with barrel 12, so that the suction pressure can be retained without the need to manually hold plunger 14 in a withdrawn position.

In accordance with this invention, lock 26 comprises a malleable and typically metal sheet 27 made of a malleable brass alloy, for example and having a thickness on the order of 0.015 to 0.03 inch. For example, FIG. 2 shows lock 26 in its original, flat configuration as a piece of flat material cut out in the shape indicated.

Lock 26 defines a cutaway portion 28 extending through the edge of sheet 27 in one area as shown and defining foldable tab means 30, 31, 32 positioned on the outer edge of sheet 27.

Cutaway portion 28 may be sized so that a syringe plunger 14, comprising radially extending vanes 16, may be placed to extend through central cutaway portion 28 as shown in FIGS. 3 and 4.

Lock 26 may be mounted on the distal flange 34 of syringe barrel 12, with tabs 30, 31, 32 being folded underneath flange 34 for retention of lock 26 thereon.

The malleable sheet 27 of lock 26 may also define a protrusion 36 extending into the area of cutaway portion 28 to serve as rotational stop means to limit rotation of the plunger.

As shown, the malleable sheet 27 which comprises syringe lock 26 may be of a generally U-shape, defining a pair of arms 38, 40. Adjacent the end of each of the arms 38, 40 resides one of tabs 30, 31, while the third tab 32 may be positioned at the end of malleable sheet 27 as opposed to the first and second tabs 30, 31.

In use, as shown in FIG. 1, syringe plunger 14 may be withdrawn to create a suction pressure or partial vacuum in barrel 12 and the bore of biopsy needle 20. When syringe plunger 14 is in the rotational position shown in FIG. 3, it can be freely advanced and withdrawn within plunger 14 in normal manner.

However, after syringe plunger 14 has been withdrawn to the desired position, it may be rotated to a position exemplified in FIG. 4. In that position, the straight edges 41, and sloping edge portion 42 of protrusion 36, defined in central cutaway portion 28, dig into the outer edges of vanes 16 of plunger 14, to cause retention of the plunger 14 and barrel 12 in a fixed, locked position relative to each. Thus the biopsy procedure can proceed in the manner previously described without the doctor having to worry about the plunger moving spontaneously forward to reduce the suction pressure.

However, when it is desired to move plunger 14 forward again, one only has to rotate it so that vanes 16 are brought out of their gripped relation with the edges 41, 42, as illustrated in FIG. 3. Then, plunger 14 may be readily advanced again, or further retracted, as desired.

Protrusion 36 serves as a stop member to limit free rotation of plunger 14 so that one cannot overrotate plunger 14, causing it to inadvertently move out of the locked position into a freely movable position. Thus, rotation of the plunger in one direction causes it to reliably lock, while rotation of the plunger in the other direction releases the locking.

Referring to the embodiment of FIG. 5, a modified version of the syringe lock is disclosed which, apart from the differences shown, is of identical structure and function to the previous embodiment.

It can be seen that while the inner edges 41 of arms 38, 40 are straight in the previous embodiment, the corresponding inner edges 41a of this embodiment ar curved. Likewise, protrusion 36a, while of similar function to protusion 36 of the previous embodiment, is of a more pointed and thinner shape.

Inwardly sloping edge portion 42a, (shown buried in locking relation in vane 16) is similar to portion 42 in the previous embodiment. However, in this embodiment only edge portion 42a digs into retentive relation with a vane 16 of plunger 14 upon clockwise rotation of the plunger, to retain the plunger in desired position. Thus plunger 14 may be rotated into and out of locking relation with greater ease than in the previous embodiment.

In summary, a lock for a syringe is provided having numerous advantages over prior art syringe locks.

The above has been offered for illustrative purposes only, and is not intended to limit the scope of the invention of this application, which is as defined in the claims below.

That which is claimed is:

1. A lock for a syringe, which comprises:
a single sheet of generally U-shape, said sheet defining a central, cutaway portion extending through the edge of said sheet, and attachment means positioned on said sheet, whereby a syringe plunger comprising radially extending vanes can be placed to extend through the central, cutaway portion, and the attachment means may be secured to a syringe barrel which carried the plunger so that rotation of the plunger in one direction causes at least one sheet edge portion defining the central, cutaway portion to dig into a vane of the plunger, to cause retention of the plunger and barrel in a fixed position relative to each other, and rotation of the retained plunger in the opposite direction frees the plunger from its retained relation, the attachment means comprising a foldable first and second tab positioned respectively at the end of each arm of saud U-shaped sheet, and a third foldable tab positioned at the end of said sheet opposed to said first and second tabs.

2. The sringe lock of claim 1 in which said sheet defines a protrusion extending into said cutaway portion to define said one sheet edge portion.

3. The syringe lock of claim 2 in which said protrusion also serves as rotational stop means to limit free rotation of the plunger.

4. The syringe lock of claim 1 in which said sheet is malleable.

5. A lock for a syringe, which comprises:

a single sheet of generally U-shape, said sheet defining a central cutaway portion extending through the edge of said sheet between the arms of said U-shaped sheet, and attachment means positioned on said whereby a syringe plunger comprising radially extending vanes can be placed to extend through the central, cutaway portion, and the attachment means may be secured to a syringe barrel which carries the plunger, so that the rotation of the plunger in one direction causes at least one sheet edge portion defining the central, cutaway portion to dig into a vane of the plunger, to cause retention of the plunger and barrel in a fixed position relative to each other, and rotation of the retained plunger in the opposite direction frees the plunger from its retained relation, the attachment means comprising a first and second foldable tab positioned respectively at the end of each arm of said U-shaped sheet, and a third foldable tab positioned at the end of said sheet opposed to said first and second tabs, said sheet also defining a protrusion extending into said cutaway portion to serve as rotational stop means to limit free rotation of the plunger.

6. The syringe lock of claim 5 in which said sheet is malleable.

7. A syringe for use with an aspirating biopsy needle which comprises a tubular syringe barrel having a large diameter open end and an opposed, small diameter open end for connection to said biospy needle, a plunger defining a slidable, sealing end member positioned with said barrel, a major portion of the length of said plunger comprising radially extending vanes; and a lock for said syringe comprising a single sheet of generally U-shape, said sheet defining a central, cutaway portion extending through the edge of said sheet, and folded tab means positioned on the outer edge of said sheet and gripping a flange defined by said syringe barrel the tab means comprising a folded first and second tab positioned respectively at the end of each arm of said U-shaped sheet, and a third folded tab positioned at the end of said sheet opposed to said first and second tabs, the major portion of said plunger comprising regularly extending vanes extending through said central, cutaway portion, whereby rotation of the plunger in one direction causes at least one edge portion of said sheet which defines the central, cutaway portion to dig into a vane of the plunger, to cause retention of the plunger and barrel in a fixed position relative to each other, and rotation of the retained plunger in the opposite direction frees the plunger from its retained relation.

8. The syringe of claim 7 in which said sheet defines a protrusion extending into said cutaway portion to define said one sheet edge portion.

9. The syringe lock of claim 8 in which said protrusion also serves as rotational stop means to limit free rotation of the plunger.

10. The syringe of claim 7 in which said sheet is malleable.

11. A syringe for use with an aspirating biopsy needle which comprises a tubular syringe barrel having a large diameter open end and an opposed small diameter open end for connection to said biopsy needle; a plunger defining a slidable sealing end member positioned within said barrel, a major portion of the length of said plunger comprising radially extending vanes; and a lock for said syringe comprising a single malleable sheet of generally U-shape, said sheet defining a central, cutaway portion extending through the edge of said sheet, said sheet having tab means folded about a flange of said syringe barrel the tab means comprising a first and second foldable tab positioned respectively at the end of each arm of said U-shaped sheet, and a third foldable tab positioned at the end of said sheet opposed to said first and second tabs, said major portion of the plunger comprising radially extending vanes extending through said central, cutaway portion of the malleable sheet, whereby rotation of the plunger in one direction causes at least one sheet edge portion defining the central, cutaway portion to dig into a vane of the plunger, to cause retention of the plunger and barrel in a fixed position relative to each other, and rotation of the retained plunger in the opposite direction frees the plunger from its retained relation, said malleable sheet defining a protrusion extending into said cutaway portion to serve as a rotational stop means to limit free rotation of the plunger.

12. The syringe of claim 11 in which an edge of said protrusion is positioned to dig into said plunger vane for retention thereof.

* * * * *